(12) United States Patent
Cantillon

(10) Patent No.: US 11,864,900 B2
(45) Date of Patent: Jan. 9, 2024

(54) ADVANCED CARDIAC WAVEFORM ANALYTICS

(71) Applicant: THE CLEVELAND CLINIC FOUNDATION, Cleveland, OH (US)

(72) Inventor: Daniel J. Cantillon, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 377 days.

(21) Appl. No.: 17/270,260

(22) PCT Filed: Aug. 20, 2019

(86) PCT No.: PCT/US2019/047141
§ 371 (c)(1),
(2) Date: Feb. 22, 2021

(87) PCT Pub. No.: WO2020/041231
PCT Pub. Date: Feb. 27, 2020

(65) Prior Publication Data
US 2021/0338139 A1    Nov. 4, 2021

Related U.S. Application Data

(60) Provisional application No. 62/720,469, filed on Aug. 21, 2018.

(51) Int. Cl.
*A61B 5/00* (2006.01)
*A61B 5/316* (2021.01)
(Continued)

(52) U.S. Cl.
CPC ............ *A61B 5/316* (2021.01); *A61B 5/0006* (2013.01); *A61B 5/0022* (2013.01); *A61B 5/256* (2021.01);
(Continued)

(58) Field of Classification Search
CPC . A61B 2560/02; A61B 5/0006; A61B 5/0022; A61B 5/256; A61B 5/316;
(Continued)

(56) References Cited

U.S. PATENT DOCUMENTS 9,149,199 B2 * 10/2015 Farazi .................. A61N 1/3622
9,161,705 B2    10/2015 Tamil et al.
(Continued)

FOREIGN PATENT DOCUMENTS

CN          107408144 A    11/2017
EP            3079571 A1   10/2016
(Continued)

OTHER PUBLICATIONS

Shen T., Sudden Cardiac Death Detection Methods Based on ECG Biometric Technologies, Shen et al., J Comput Eng Inf Technol 2016, S1 http://dx.doi.org/10.4172/2324-9307.S1-002.
(Continued)

*Primary Examiner* — George Manuel
(74) *Attorney, Agent, or Firm* — TAROLLI, SUNDHEIM, COVELL & TUMMINO L.L.P.

(57) ABSTRACT

This disclosure describes systems and methods for electrocardiographic waveform analysis, data presentation and actionable advisory generation. Electrocardiographic waveform data can be received from a wearable device associated with a patient. A mathematical analysis can be performed on the electrocardiographic waveform data to provide cardiac analytics. A visualization of the cardiac analytics on a dashboard display can be generated. A value can be based on a comparison of the cardiac analytics to at least one baseline value for the patient; and a decision of whether or not to generate an actionable advisory for the electrocardiographic waveform data can be made based on the value. When the actionable advisory is generated, the actionable advisory is (Continued)

sent to one or more medical professionals, where it can be modified, and displayed with the visualization of the cardiac analytics.

20 Claims, 4 Drawing Sheets

(51) Int. Cl.
*A61B 5/363* (2021.01)
*A61B 5/364* (2021.01)
*G16H 50/20* (2018.01)
*A61B 5/35* (2021.01)
*A61B 5/256* (2021.01)
*A61B 5/36* (2021.01)
*A61B 5/366* (2021.01)
*A61B 5/353* (2021.01)

(52) U.S. Cl.
CPC .............. *A61B 5/35* (2021.01); *A61B 5/353* (2021.01); *A61B 5/36* (2021.01); *A61B 5/363* (2021.01); *A61B 5/364* (2021.01); *A61B 5/366* (2021.01); *A61B 5/6801* (2013.01); *A61B 5/742* (2013.01); *A61B 5/743* (2013.01); *A61B 5/7405* (2013.01); *A61B 5/746* (2013.01); *A61B 5/747* (2013.01); *A61B 5/7455* (2013.01); *G16H 50/20* (2018.01); *A61B 2560/02* (2013.01)

(58) Field of Classification Search
CPC ........... A61B 5/349; A61B 5/35; A61B 5/353; A61B 5/36; A61B 5/363; A61B 5/364; A61B 5/366; A61B 5/6801; A61B 5/7264; A61B 5/7405; A61B 5/742; A61B 5/743; A61B 5/7455; A61B 5/746; A61B 5/747; G16H 50/20

See application file for complete search history.

(56) References Cited

U.S. PATENT DOCUMENTS

| | | |
|---|---|---|
| 2012/0095520 A1 | 4/2012 | Zhang et al. |
| 2013/0231947 A1 | 9/2013 | Shusterman |
| 2015/0164349 A1 | 6/2015 | Gopalakrishnan |
| 2015/0164410 A1* | 6/2015 | Selvaraj ............... A61B 5/316 600/509 |
| 2015/0265164 A1 | 9/2015 | Gopalakrishnan |
| 2016/0135706 A1 | 5/2016 | Sullivan |
| 2016/0278659 A1 | 9/2016 | Kaib |
| 2017/0238814 A1 | 8/2017 | Gopalakrishnan |
| 2018/0325410 A1 | 11/2018 | Kaib et al. |
| 2019/0038149 A1 | 7/2019 | Gopalakrishnan |
| 2019/0216350 A1 | 7/2019 | Sullivan et al. |
| 2019/0298214 A1 | 10/2019 | Kaib et al. |

FOREIGN PATENT DOCUMENTS

| | | |
|---|---|---|
| EP | 3204881 A1 | 8/2017 |
| JP | 2011062367 A | 3/2011 |
| JP | 2017500093 A | 1/2017 |
| JP | 2018503885 A | 8/2018 |
| WO | 20100054088 A1 | 5/2010 |
| WO | 2015002945 A2 | 1/2015 |
| WO | 20150089484 A1 | 6/2015 |
| WO | 2016077786 A1 | 5/2016 |
| WO | 2016160549 A1 | 6/2016 |

OTHER PUBLICATIONS

PCT Search Report and Written Opinion for corresponding Application Serial No. PCT/US2019/047141, dated Nov. 4, 2019, pp. 1-11.
Notice of Office Action and its English translation for Japanese Patent Application No. 2021-510052, dated May 6, 2022.
Australian Exam Report for Corresponding Application Serial No. 2019326399, dated Jan. 25, 2023, pp. 1-6.

* cited by examiner

ADVANCED CARDIAC WAVEFORM ANALYTICS

RELATED APPLICATIONS

This application claims the benefit of U.S. Provisional Application No. 62/720,469, entitled "ADVANCED CARDIAC WAVEFORM ANALYTICS," filed Aug. 21, 2018. The entirety of this application is hereby incorporated by reference for all purposes.

TECHNICAL FIELD

The present disclosure relates generally to advanced cardiac waveform analytics (ACWA) and, more specifically, to systems and methods for electrocardiographic waveform analysis, data presentation and actionable advisory generation.

BACKGROUND

Electrocardiography is a process of recording electrocardiographic waveforms from a patient's heart. The first known recording of electrocardiographic waveforms was obtained from the human body surface using galvanizing skin electrodes in the early $20^{th}$ century. Since this first known recording, scientific advances have increased the diagnostic value of electrocardiographic waveforms for cardiovascular disorders. However, contemporary diagnostic tools using electrocardiographic waveforms provide only limited analytic capabilities that do not routinely incorporate important changes in cardiac repolarization, and do not effectively account for confounding physiologic variables including sex, time of day, the presence of baseline abnormalities and individual heart rate variance—thereby limiting contextual interpretation for a given patient. In addition, contemporary tools provide very limited output displays and lack a dynamic tool for the purposes of exchanging, highlighting, annotating and editing key data elements according to clinical relevance for concise export into the electronic medical record.

Add to this the fact that over 90% of telemetry alarms do not elicit nor merit clinical responses from bedside health care providers, while up to 44% of cardiopulmonary arrests (CPAs) are not detected appropriately. Only approximately 1 in 4 patients survive an in hospital CPA according to survival statistics from the American Heart Association. However, advances in non-invasive cardiovascular risk stratification modalities have emerged, including ECG-based methods for real-time detection of cardiac arrhythmias for patients undergoing continuous cardiac rhythm monitoring (CCRM). Unfortunately, no cohesive methodology exists for the collection, processing, analytics and mobile distribution of the CCRM data to provide advanced warning of sustained atrial or ventricular tachyarrhythmias, cardiopulmonary arrest, critical metabolic derangements or impending heart failure deterioration.

SUMMARY

The present disclosure relates generally to advanced cardiac waveform analytics (ACWA), a method for the collection, processing, analysis and mobile management of cardiac waveform data applying advanced risk stratification tools for advance warning of cardiac arrhythmias, including cardiopulmonary arrest, heart failure decompensation and critical metabolic derangements. Notably, ACWA can account for not only electrocardiographic waveform data, but also can account for physiologic confounding variables. More specifically, the present disclosure relates to systems and methods for electrocardiographic waveform analysis, data presentation and actionable advisory generation.

In one aspect, the present disclosure includes a system that can perform waveform analysis, data presentation, and actionable advisory generation. The system includes a non-transitory memory configured to store instructions and a processor to execute the instructions to receive electrocardiographic waveform data from a wearable device associated with a patient, perform a mathematical analysis of the electrocardiographic waveform data to provide cardiac analytics; generate a visualization of the cardiac analytics; provide a value based on a comparison of the cardiac analytics to at least one baseline value for the patient; decide whether or not to generate an actionable advisory for the electrocardiographic waveform data based on the value; and alter the visualization based on the decision of whether or not to generate the actionable advisory. The system also includes a wireless transceiver to transmit the visualization to one or more medical professionals.

In another aspect, the present disclosure includes a method for electrocardiographic waveform analysis, data presentation and actionable advisory generation. The method can be performed by a system comprising a processor. The method can include receiving electrocardiographic waveform data from a wearable device associated with a patient; performing a mathematical analysis of the electrocardiographic waveform data to provide cardiac analytics; generating a visualization of the cardiac analytics on a dashboard display; providing a value based on a comparison of the cardiac analytics to at least one baseline value for the patient; and deciding, by the system, whether or not to generate an actionable advisory for the electrocardiographic waveform data based on the value. When the actionable advisory is generated, the actionable advisory is sent to one or more medical professionals and displayed with the visualization of the cardiac analytics.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
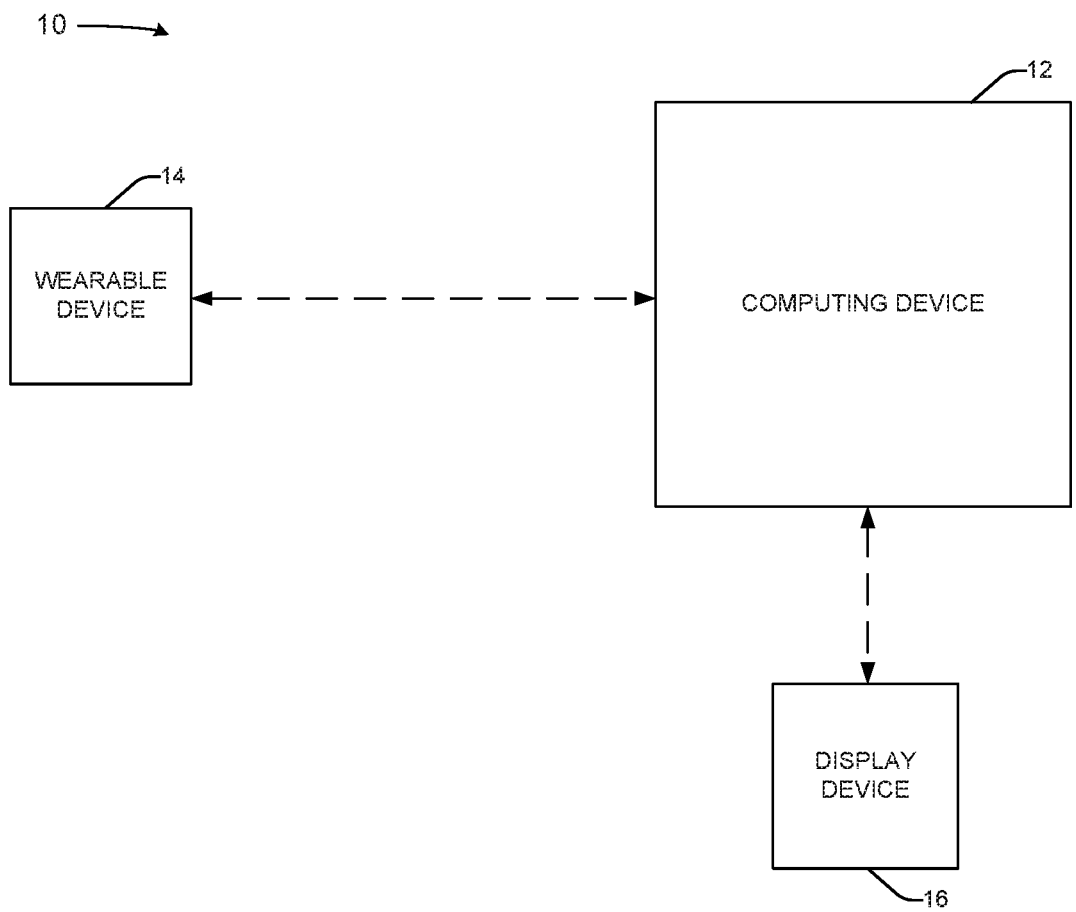
FIG. 1 is a block diagram showing an example of a system that can perform advanced cardiac waveform analytics (ACWA) in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the term "Advanced Cardiac Waveform Analytics (ACWA)" can refer to an analysis tool, or the use of an analysis tool, for electrocardiographic waveform analysis, data presentation and actionable advisory generation. The analysis tool of ACWA can be specific to an individual patient. ACWA can also refer to the method for the collection, processing, analysis and mobile management of cardiac waveform data applying advanced risk stratification tools for advance warning of cardiac arrhythmias.

As used herein, the term "electrocardiography (ECG or EKG)" can refer to the process of recording the electrical activity of a patient's heart over a period of time using single or multiple electrodes placed on the patient's skin. The electrodes detect low amplitude electrical changes on the skin that arise from the heart muscle's electrophysiologic pattern of depolarizing and repolarizing during each heartbeat.

As used herein, the term "electrocardiographic waveform" can refer to the plotted tracing of recorded electrical signals from the single or multiple surface skin electrodes (Y-axis) per unit time (X-axis). The electrocardiographic waveform can be collected by a wearable device associated with a patient.

As used herein, the term "electrocardiographic waveform data" can refer to values encapsulated within the electrocardiographic waveform.

As used herein, the term "wearable device" can refer to a technology that can collect electrocardiographic waveforms that is worn on or near a patient's body.

As used herein, the term "cardiac cycle" can refer to the physical contraction and relaxation of the heart chambers during systole and diastole, along with the accompanying changes in blood flow and blood pressure within the heart and in the blood vessels leading to and from the heart. The cardiac cycle can also refer to the electrocardiographic waveform data elements associated with the electrical depolarization and repolarization of the heart during systole and diastole (e.g., a heartbeat). For each single heartbeat, the electrocardiographic waveform can show P, Q, R, S, and T portions. The QRS portions together can make up the QRS complex. The cardiac cycle can include data elements associated with the human cardiac atria (PR interval) and the human cardiac ventricles (QRS interval, QT interval, RT interval).

As used herein, the term "physiological confounding variable" can refer to an extraneous variable whose presence affects the variables being studied so that the results do not reflect the actual relationship between the variables. Examples of physiological confounding variables include sex, time of day, the presence of baseline abnormalities, specific medication exposures, individual heart rate variance, and the like.

As used herein, the term "cardiac analysis" can refer to direct measurement of electrocardiographic waveform data over the cardiac cycle, and mathematical analysis of the electrocardiographic waveform data. In some instances, the cardiac analysis can account for the presence of physiological confounding variables. Cardiac analysis can include continuous and categorical descriptive reporting of the at least a portion of the electrocardiographic waveform and any calculated values according to the mathematical analysis.

As used herein, the term "mathematical analysis" can refer to the application of mathematics to data (e.g., at least a portion of the electrocardiography waveform data, such as for one or more cardiac cycles). For example, the mathematics applied can include, but is not limited to, linear or logistic regression analysis of the graphical curves, mathematical derivatives (e.g., areas under the curve) involving pre-specified time series data, and comparisons between real-time and stored fiduciary X, Y coordinates from the electrocardiographic cardiac waveform over the cardiac cycle.

As used herein, the term "machine learning" can refer to software code, routines, and/or methods the computing device and/or rules engine is self-modify to better associate specific data patterns, including trends, among candidate variables of interest with specific outcomes or clinical findings of interest to determine the probability or likelihood for the specific clinical outcome or occurrence when presented with a similar data pattern or trend. For example, a machine learning application will identify the probability or likelihood of a life-threatening cardiac arrhythmia thru the recognition of a particular data pattern that had been previously associated with this event during a training phase of the machine learning process by which the code had been modified over time, and thru repetition, to associate specific patterns within the ECG waveform with a high probability of serious life-threatening cardiac arrhythmia.

As used herein, the term "dashboard display" can refer to a graphical user interface to display analyzed cardiac data, results of mathematical analysis, real-time and/or stored electrocardiographic waveform data elements and associated values, and the like.

As used herein, the term "actionable advisory" can refer to a warning related to the patient of a clinically relevant event based on the cardiac analysis. The actionable advisory can comprise visual, auditory and tactile elements alerting the receiver of an impending clinical event, as generated by a computing device. The actionable advisory can include, but is not limited to, graphical display, text and numerical value elements transmitted to a display device. The actionable advisory can indicate a variety of clinical events, conditions and disease states, including but not limited to an atrial or ventricular arrhythmia event, congestive heart failure status, impending cardiopulmonary arrest, deterioration of heart failure status, acute coronary syndrome, or clinically important electrolyte derangements or metabolic disturbances in the human body. The actionable advisory can be inserted into the patient's electronic medical record at a given time stamp, placed within a graphical user interface display for review by the end user, or urgently communicated to the end user via audible or text messaged alert.

As used herein, the term "modified actionable advisory" can refer to an actionable advisory that has been altered, modified or otherwise acted upon by a user for re-transmission to another end user for the purposes of highlighting, annotating or exchanging clinically relevant information. The modified actionable advisory can be inserted into the patient's electronic medical record with the actionable advisory at its own given time stamp, and re-transmitted to other medical professionals.

As used herein, the term "electronic medical record (EMR)" can refer to a digital version of a patient's medical history, to be viewed, edited, and added to by medical professionals.

As used herein, the term "time stamp" can refer to a digital record of the time of occurrence of a particular event.

As used herein, the term "baseline" can refer to an average value for a certain parameter. The baseline can be patient-specific, population-specific, or the like.

As used herein, the term "clinically relevant event" can refer to any type of adverse and/or disease-related occurrence that is considered serious (exceeding defined values). Clinically relevant events can be different for different patients.

As used herein, the term "rules engine" can refer to a system that uses rules that each have a condition and an action. In operation, the rules engine can run through all the rules, pick the rules for which a condition is true, and then evaluates the corresponding actions.

As used herein, the term "alarm" can refer to a signal alerting a user. The alarm can be tactilely, auditorily, and/or visually perceptible by a user using touch, hearing, and/or sight, respectively.

As used herein, the term "automated" can refer to being operated automatically without (or with limited) human interference.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The subject can be waiting for, undergoing, or in need of medical care.

As used herein, the term "medical professional" can refer to a person providing medical care. A medical professional can be a doctor, a nurse, a nurse practitioner, an emergency medical technician, or any other type of trained caregiver.

As used herein, the term "threshold" can refer to any predetermined value defined as the limit for a particular quantifiable phenomenon; any measured value above or below this limit can initiate a signal, alarm, message or other form of communication to be sent to systems and users capable of response.

II. Overview

The present disclosure relates generally to advanced cardiac waveform analytics (ACWA) and, more specifically, to systems and methods for electrocardiographic waveform analysis, data presentation and actionable advisory generation. The systems and methods can be used to generate actionable advisories for cardiac maladies, including (but not limited to) cardiac arrhythmias, heart failure, impending cardiopulmonary arrest, acute coronary syndrome or critical metabolic abnormalities. Notably, the ACWA can account for physiologic confounding variables when determining when to issue the actionable advisories. Additionally, the present disclosure includes a communication tool by which the displayed actionable advisory can be highlighted, edited, annotated and exchanged by medical professionals and exported to an electronic medical record system according to clinical relevancy.

III. Systems

One aspect of the present disclosure can include a system 10 (FIG. 1) that can perform advanced cardiac waveform analytics (ACWA). The system 10 can perform electrocardiographic waveform analysis, data presentation and actionable advisory generation. The systems 10 can generate actionable advisories for cardiac maladies, including (but not limited to) cardiac arrhythmias, heart failure, impending cardiopulmonary arrest, acute coronary syndrome or critical metabolic abnormalities. Notably, the system 10 can account for physiologic confounding variables when determining when to issue the actionable advisories. Additionally, the present disclosure includes a communication tool by which the displayed actionable advisory can be highlighted, edited, annotated and exchanged by medical professionals, shared/discussed with patients, and exported to an electronic medical record system according to clinical relevancy.

The system 10 (FIG. 1) can include a computing device 12, which can be in communication with a wearable device 14 and a display device 16. The wearable device 14 can be associated with a patient. The wearable device 14 can be coupled to one or more electrodes that can collect electrocardiographic data. For example, electrocardiographic data can be continuously recorded and collected from surface skin electrodes. The wearable device 14 can send the electrocardiographic data to the computing device 12. The computing device 12 can perform ACWA on the electrocardiographic data and send a visualization of one or more cardiac analytics (e.g., wavelets) to the display device 16. The computing device 12 can also send actionable advisories to the display device 16. The actionable advisory itself can be an unalterable insertion into the patient's EMR at a given time-stamp, which can be transmitted to the display device 16. Medical professionals can receive mobile device communications on the display device 16 analogous to a text message or push notification with visual, audible, and/or vibratory alert. The display device 16 can be associated with one or more medical professionals and can allow actions to be performed on the actionable advisories, thereby creating modified actionable advisories. For example, the display device 16 can be associated with an input mechanism (e.g., a touch screen, a keyboard, a mouse, or the like). Medical professionals can send the modified actionable advisory to other medical professionals (e.g., for doctors to give a second opinion, for emergency response professionals to take action on the patient, for a physician-in-training to exchange the actionable advisory or modified actionable advisory with an attending physician outside the hospital, for a non-cardiac physician to send the actionable advisory to a cardiologist for review and to receive an modified actionable advisory, etc.). The computing device 12 can send the actionable advisories and/or modifications to the actionable advisories to an electronic medical record associated with the patient with respective time stamps. The modified actionable advisories can be tracked much in the same manner as shared-space document editing; one may easily revert to the original actionable advisory or to previous versions of modified actionable advisories. Additionally, the computing device 12 can also transmit other elements to the electronic medical record, such as those which led to the generation of the actionable advisory.

Figure 2:
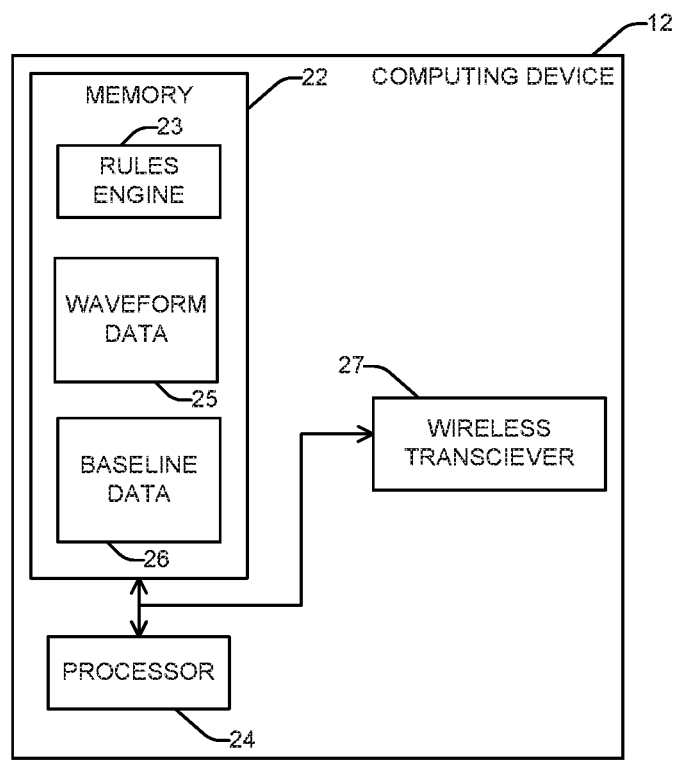
FIG. 2 is a block diagram showing an example of a computing device that can be used in the system of FIG. 1 to perform waveform analysis, data presentation, and actionable advisory generation.

The computing device 12 is shown in more detail in FIG. 2. However, FIG. 2 does not show the complete detail of the computing device 12. The computing device 12 can include a non-transitory memory 22 configured to store instructions to implement a rules engine 23 and data. The computing device 12 can also include a processor 24 that can access the non-transitory memory 22 and execute the instructions to implement the rules engine 23. The non-transitory memory 22 can also store data, including electrocardiographic waveform data 25 (which can include cardiac analytics) and baseline data 26. The computing device 12 can include a wireless transmitter 27, which can allow communication with the wearable device 14, the display device 16, and the electronic medical record (not shown). The wireless transmitter can communicate according to one or more protocols, including Bluetooth, cellular, WiFi, or the like. In some instances, the computing device 12 can also include a wired connection for data transmission.

Figure 3:
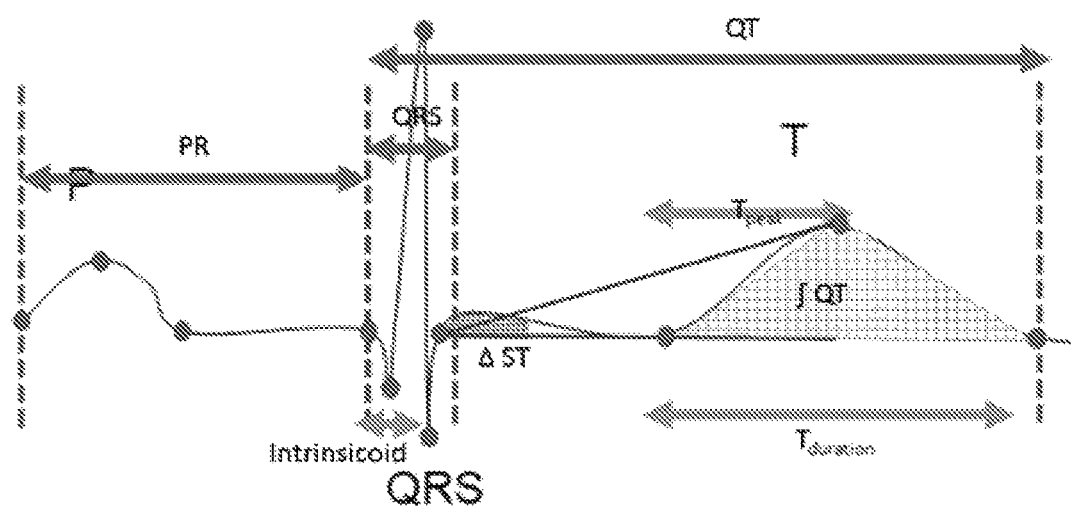
FIG. 3 is an example of a cardiac cycle showing different cycle measurements and derivations that may be needed to perform ACWA.

In operation, the computing device 12 can receive electrocardiographic waveform data from the wearable device 14 associated with the patient. The computing device 12 can perform a mathematical analysis of the electrocardiographic waveform data 25 to provide cardiac analytics. For example, the cardiac analytics can be wavelets taken from the electrocardiographic waveform data 25 (either from a single cardiac cycle or a plurality of cardiac cycles). Examples of different parts of the electrocardiographic waveform data 25 are shown in FIG. 3. The cardiac analytics can include, but are not limited to, a PR interval, an RR interval, an RT interval, a QRS duration time interval, an intrinsicoid time interval, a QT time interval, a corrected QT interval, a modified moving average of the QT interval, a T-peak amplitude voltage (as a highest absolute value of T maximum to T minimum voltage), a T-peak-to-terminus time interval, an ST angle as a linear regression of a ST segment, a measurement of ST amplitude change from baseline, QRS and QT waveform tracings, a percentage of X,Y coordinates aligning with a patient-specific template for the QRS waveform morphology, a percentage of X,Y coordinates aligning with a patient-specific template for the QT waveform morphology, and an area under the curve of the X,Y plot for the QT-waveform morphology. In each case, the cardiac analytics are determined automatically according to automated cardiac waveform analysis procedures. A visualization of the cardiac analytics can be generated and sent to the display device.

The rules engine 23 of the computing device 12 can perform a comparison between the cardiac analytics and the stored baseline data 26. The stored baseline data 26 can be specific to the patient (e.g., generated based on initially submitted data from the patient), which can ameliorate the effects of physiologic confounding variables. Enhanced sensitivity is achieved by each patient serving as his or her own control, in which percentage deviations from established norms and combination of the weighted metrics, using the patient-specific template and allowed normal ranges derived by the continuously collected clock-based data (e.g., showing temporal variation), are incorporated. Thus, both the individual waveform wavelet and the running trend for the important measurements can be analyzed continuously. In addition, the parameters for generating an actionable advisory can be indication-specific.

In some instances, the baseline data 26 to be used by the rules engine 23 can include population data for either patients similar to the patient (e.g., age, sex, severity of illness, weight, etc.) or for the population in general. This may be especially relevant in cases in which the patient is known or suspected to have an abnormal electrocardiograph due to a pathological disease state at the initiation of cardiac monitoring. In this scenario, the computing device 12 can select a 'normal' waveform template derived from population data matched according to the easily identified variables known to influence the normal cardiac waveform, including age, sex, race and body mass index, entered at the time of monitoring initiation. If a non-patient specific 'normal' waveform is a poor match and generates excessive alarms at baseline, then the computing device 12 can allow suspension of the wavelet-based analytics until re-activated. A 'snooze' feature can be programmed to re-activate after a specified period of time unless programmed otherwise. The non-wavelet basic and advanced analytics can continue to operate while wavelet match is suspended.

The rules engine 23 can perform a series of logical comparisons (e.g., one or more wavelet comparisons) between the cardiac analytics and the baseline values. The rules engine 23 can provide a value based on the comparison of one or more wavelets. The value can indicate a clinically relevant state, such as the presence or absence of a general or specific cardiac pathology. A decision can be made by the rules engine 23 whether or not to generate an actionable advisory for the electrocardiographic waveform data based on the value. When the actionable advisory is generated, it is sent to the display device 16 in connection with a tactile, audio, or visual alarm. At least one of the electrocardiographic data, the cardiac analytics, the value, and/or the actionable advisory can be transmitted to an electronic health record associated with the patient (each associated with a time stamp).

As an example, the rules engine 23 can perform both categorical and continuous variable analysis of the stored QT and RT interval data that is continuously collected and reported on a dashboard user interface radial display in a 24 hour time domain. Within this context, significant deviation from baseline values and/or violation of specific absolute values can trigger a series of rules engine and logic comparisons by which the R-T measurement on a number of heart beats collected within a beat buffer sample are measured and analyzed for the concomitant presence of ventricular ectopic heart beats and/or ventricular tachycardia and the precise coupling intervals on the R-T time measurement are compared with the R-R interval for the abnormal beats when determining to generate an actionable advisory specific to the presence of pathologic QT prolongation with a high probability for serious life-threatening ventricular cardiac arrhythmias. The rules engine 23 may also incorporate other clinical variables of interest and/or physiologic confounding variables. Each patient is their own control, and the morphologic features are compared with the stored template in real-time.

The present disclosure may provide complete (or semi-complete) automation of the continuous cardiac rhythm monitoring process, removing the need for human electrocardiographic assessment and review of ACWA-generated actionable advisories prior to their insertion into the patient's medical record. Advanced pattern-recognition programs and/or machine learning algorithms, as implemented by the ACWA, may allow for a fully automated cardiac monitoring system, limiting the potential for human error and enhancing the ability to identify subtle, high-risk cardiac rhythm patterns. Short of complete automation, the system 10 can mitigate the eventuality of introduced human error.

IV. Methods

Another aspect of the present disclosure can include a method 40 (FIG. 4) for performing advanced cardiac waveform analytics (ACWA). The method 40 is illustrated as a process flow diagram with flowchart illustrations. For purposes of simplicity, the method 40 is shown and described as being executed serially; however, it is to be understood and appreciated that the present disclosure is not limited by the illustrated order, as some steps could occur in different orders and/or concurrently with other steps shown and described herein. Moreover, not all illustrated aspects may be required to implement the method 40.

The method 40 can be executed by hardware—for example, the method 40 can be performed primarily by the computing device 12 of the system 10 of FIG. 1. One or more hardware elements of the computing device 12 of system 10 can execute software routines to implement at least a portion of the method 40. Additionally, one or more elements of the computing device 12 of system 10 can include a non-transitory memory 22 storing the software routines and one or more processors 24 to execute the software routines corresponding to at least the portion of the method 40. Other components (wearable device 14, display device 16, etc.) of the system 10 of FIG. 1 may also be used to facilitate the method 40.

Figure 4:
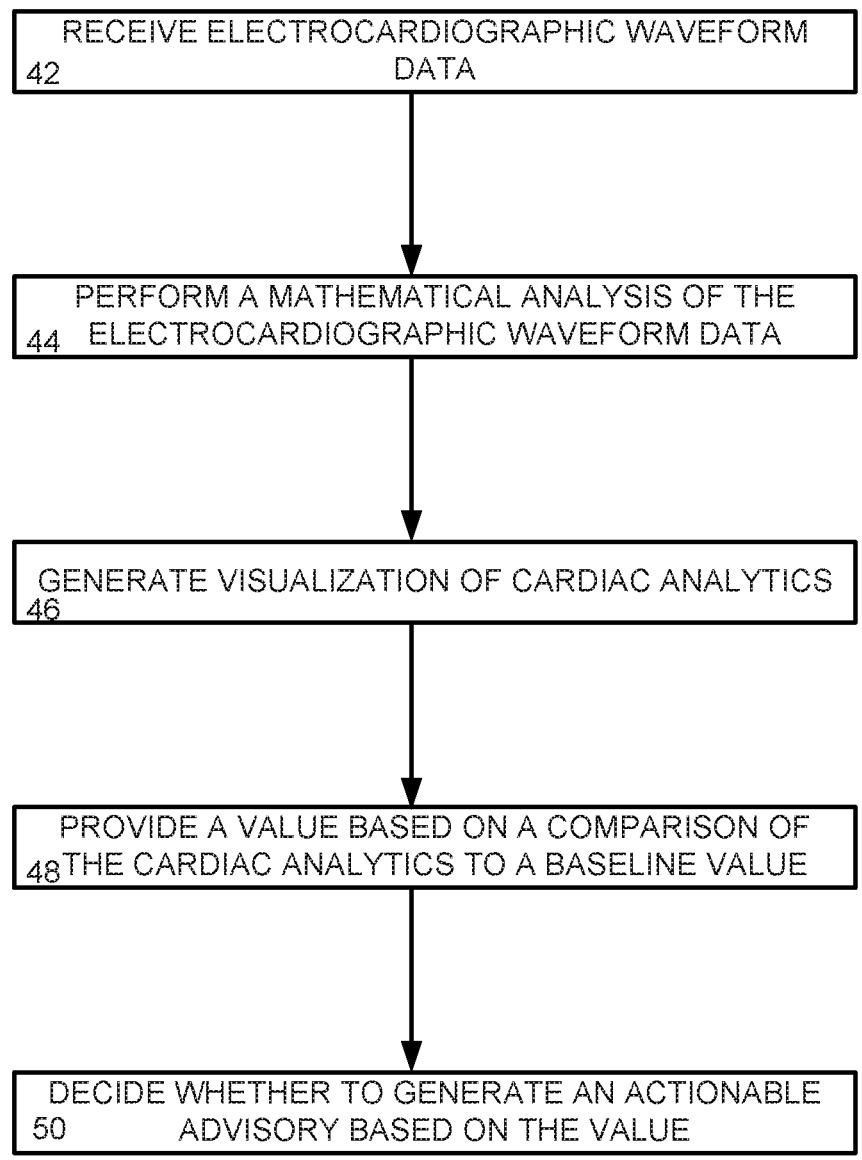
FIG. 4 is a process flow diagram illustrating a method for performing ACWA in accordance with another aspect of the present disclosure.

At 42 of FIG. 4, electrocardiographic waveform data can be received. The electrocardiographic waveform data can be recorded by one or more skin surface electrodes and transmitted by a wearable device (e.g., wearable device 14) associated with a patient. At 44, a mathematical analysis can be performed on the electrocardiographic waveform data. For example, specific features of the electrocardiographic waveform can be isolated and pulled from the entire electrocardiographic waveform (one or more cardiac cycles). Based on the mathematical analysis, one or more cardiac analytics can be provided.

At 46, a visualization of cardiac analytics can be generated. The visualization can be generated, for example, on a dashboard display. The visualization can be sent to a display device (e.g., display device 16) to be displayed to (and/or used by) a medical professional. The cardiac analytics can also be associated with the patient and sent to an electronic medical record of the patient with a time stamp.

At 48, a value can be provided based on a comparison of the cardiac analytics to a baseline value. For example, the comparison can be based on a correlation between the electrocardiographic waveform and at least one baseline value, wavelet-matching between the electrocardiographic waveform and the baseline waveform, and/or a specific alteration of any of the cardiac cycle measurement associated with a clinically relevant event. The baseline value can be a patient-specific baseline value. However, in other instances, the baseline value can be for patients similarly situated (e.g., same sex, same weight, same age, etc.). In other instances, the baseline value can be one for the population in general. The computing device can use a rules engine (e.g. rules engine 23) to apply a series of logical comparisons between the electrocardiographic waveform data and the baseline value, which can be stored in or accessed by the rules engine. Based on the comparisons by the rules engine, the value can be generated. The value can account for physiologic confounding variables due to the specially-selected baseline value. The rules engine can determine whether the value indicates a disease state or a non-disease state. In some instances, the value can be sent to the electronic medical record associated with the patient, and/or the value can be sent to a dashboard display or, in other instances, another graphical user interface for display as a tile or icon to denote a clinically relevant event.

At 50, a decision can be made as to whether an actionable advisory will be generated based on the value. The decision can be based on whether the value satisfies a threshold (e.g., the disease state and//or a change in the disease state). The decision, in some instances, can be sent to the electronic medical record associated with the patient. The actionable advisories can be for one or more cardiac maladies, including (but not limited to) cardiac arrhythmias, heart failure, impending cardiopulmonary arrest, acute coronary syndrome or critical metabolic abnormalities. When the actionable advisory is generated, the actionable advisory can be sent to one or more medical professionals (e.g., via a messaging program) and displayed with the visualization of the cardiac analytics (e.g., on the display device 16). The actionable advisory can be accompanied by a tactile, audio, or visual alarm. The actionable advisory can be highlighted, edited, annotated and exchanged by medical professionals and sent back to the computing device 12.

A modified actionable advisory and/or the annotation to the actionable advisory can be received and/or generated (e.g., by computing device 12). The computing device 12 can send the modified actionable advisory to an electronic medical record system and link the modified actionable advisory to the original actionable advisory. In the electronic medical record, different actionable advisories can be displayed in order of relevance. The modified actionable advisory can be sent by the computing device 12 to other medical professionals. For example, the medical professionals can send the modified actionable advisory to other medical professionals (e.g., for doctors to give a second opinion, for emergency response professionals to take action on the patient, for a physician-in-training to exchange the actionable advisory or modified actionable advisory with an attending physician outside the hospital, for a non-cardiac physician to send the actionable advisory to a cardiologist for review and to receive an modified actionable advisory, etc.).

From the above description, those skilled in the art will perceive improvements, changes and modifications. Such improvements, changes and modifications are within the skill of one in the art and are intended to be covered by the appended claims.

What is claimed is:

1. A method comprising:
   receiving, by a system comprising a processor, electrocardiographic waveform data from a wearable device associated with a patient;
   performing, by the system, a mathematical analysis of the electrocardiographic waveform data to provide cardiac analytics, wherein the cardiac analytics are templates taken from the electrocardiographic waveform data;
   generating, by the system, a visualization of the cardiac analytics on a dashboard display;
   providing, by the system, a value based on a comparison of the cardiac analytics to at least one baseline value for the patient, wherein the value indicates a clinically relevant state;
   deciding, by the system, whether or not to generate an actionable advisory for the electrocardiographic waveform data based on the value, wherein the decision is based on whether the value satisfies a threshold for the electrocardiographic waveform data, and wherein the actionable advisory is a warning of a clinically relevant event for the patient;
   altering, by the system, the visualization of the cardiac analytics on the dashboard display based on the decision of whether or not to generate the actionable advisory; and
   when the actionable advisory is generated, sending, by the system, the actionable advisory to one or more medical professionals and displaying, by the system, the actionable advisory with the visualization of the cardiac analytics.

2. The method of claim 1, further comprising performing, by the system, a machine learning analysis of the electrocardiographic waveform data and one or more physiologic confounding variables in associated with the value exceeding the threshold.

3. The method of claim 1, further comprising:
receiving, by the system, a modification to the actionable advisory from at least one medical professional;
generating, by the system, a modified actionable advisory based on the modification; and
altering, by the system, the visualization of the cardiac analytics on the dashboard display to include a display of the modified actionable advisory.

4. The method of claim 3, further comprising sending, by the system, the modified actionable advisory to the one or more medical professionals.

5. A method comprising:
receiving, by a system comprising a processor, electrocardiographic waveform data from a wearable device associated with a patient;
performing, by the system, a mathematical analysis of the electrocardiographic waveform data to provide cardiac analytics, wherein the mathematical analysis comprises:
  obtaining time intervals including at least one of a PR interval, an RR interval, an ORS duration time interval, an intrinsicoid time interval, an RT interval, and a QT time interval;
  performing automated procedures to calculate a corrected QT interval, a corrected RT interval, a modified moving average of the QT interval, and a modified moving average of the RT interval;
  obtaining a T-peak amplitude voltage as a highest absolute value of T maximum to T minimum voltage, and a T-peak-to-terminus time interval;
  obtaining ST angle as a linear regression of a ST segment, change in ST amplitude voltage from baseline;
  measuring X, Y plotted coordinates of the ORS, QT and RT waveform tracings;
  calculating a percentage of X, Y coordinates aligning with a patient- specific template for the ORS waveform morphology;
  calculating a percentage of X, Y coordinates aligning with a patient- specific template for the QT or RT waveform morphology; or
  measuring an area under the curve of the X, Y plot for the QT-waveform morphology;
generating, by the system, a visualization of the cardiac analytics on a dashboard display;
providing, by the system, a value based on a comparison of the cardiac analytics to at least one baseline value for the patient;
generating an actionable advisory, by the system, based on a value exceeding threshold for the electrocardiographic waveform data; and
not generating an actionable advisory, by the system, based on a value not exceeding threshold for the electrocardiographic waveform data;
  wherein when the actionable advisory is generated, the actionable advisory is sent to one or more medical professionals and displayed with the visualization of the cardiac analytics.

6. The method of claim 1, further comprising at least one of acquiring and storing, by the system, patient-specific baseline values as a comparison template for the electrocardiographic waveform data.

7. The method of claim 1, wherein the providing further comprises applying a series of logical comparisons between the electrocardiographic waveform data and the at least one baseline value defined in a rules engine.

8. The method of claim 1, wherein when the actionable advisory is generated, the visualization is accompanied by a tactile, audio, or visual alarm.

9. The method of claim 1, wherein at least one of the electrocardiographic waveform data, the value, and the decision are transmitted to an electronic health record associated with the patient.

10. A system comprising:
a non-transitory memory storing instructions; and
a processor to execute the instructions to:
  receive electrocardiographic waveform data from a wearable device associated with a patient;
  perform a mathematical analysis of the electrocardiographic waveform data to provide cardiac analytics, wherein the cardiac analytics are templates taken from the electrocardiographic waveform data;
  generate a visualization of the cardiac analytics on a dashboard display;
  provide a value based on a comparison of the cardiac analytics to at least one baseline value for the patient, wherein the value indicates a clinically relevant state;
  decide whether or not to generate an actionable advisory for the electrocardiographic waveform data based on the value, wherein the decision is based on whether the value satisfies a threshold for the electrocardiographic waveform data, and wherein the actionable advisory is a warning of a clinically relevant event for the patient; and
  alter the visualization of the cardiac analytics on the dashboard display based on the decision of whether or not to generate the actionable advisory,
  wherein when the actionable advisory is generated the actionable advisory is displayed with the visualization of the cardiac analytics; and
a wireless transceiver to transmit the actionable advisory and the visualization of the cardiac analytics to one or more medical professionals.

11. The system of claim 10, wherein the visualization of the cardiac analytics and the actionable advisory are sent to one or more display devices associated with one or more medical professionals.

12. The system of claim 11, wherein the one or more display devices comprises an input mechanism, which allows the one or more medical professional to annotate the visualization and the actionable advisory.

13. The system of claim 10, wherein the comparison is based on application of a series of logical comparisons between the electrocardiographic waveform data and the at least one baseline value.

14. The system of claim 10, wherein when the actionable advisory is generated, the visualization is accompanied by a tactile, audio, or visual alarm.

15. The system of claim 10, wherein at least one of the electrocardiographic data, the cardiac analytics, the value, and the decision are transmitted to an electronic health record associated with the patient.

16. The system of claim 10, wherein the processor is further configured to execute the instructions to:
receive initial data from the patient; and
determine the at least one baseline value based on the initial data from the patient.

17. The system of claim 10, wherein in response to the alteration of a visualization by a user, the system receives an annotated, reviewed, highlighted, or exchanged modified actionable advisory and displays the modified actionable advisory.

18. The system of claim 17, wherein the processor further executes the instructions to send the modified actionable advisory to an electronic medical record associated with the patient with a time stamp.

19. The system of claim 10, wherein the mathematical analysis comprises automated cardiac waveform analysis procedures of portions of the electrocardiographic waveform data.

20. The system of claim 10, wherein the wireless transceiver is configured with at least one of cellular, Bluetooth, and WiFi transmission capabilities.

* * * * *